United States Patent [19]

Hartmann et al.

[11] Patent Number: 4,844,886
[45] Date of Patent: Jul. 4, 1989

[54] COSMETIC COMPOSITIONS WITH A CONTENT OF HYDROGENPEROXIDE AND ALPHA-BISABOLOL AS WELL AS USE OF ALPHA-BISABOLOL FOR THE STABILIZATION OF HYDROGENPEROXIDE

[75] Inventors: Peter Hartmann, Darmstadt; Joachim Köhler, Reinheim, both of Fed. Rep. of Germany

[73] Assignee: Wella Aktiengesellschaft, Darmstadt, Fed. Rep. of Germany

[21] Appl. No.: 165,277
[22] PCT Filed: Jun. 25, 1987
[86] PCT No.: PCT/EP87/00342
§ 371 Date: Mar. 2, 1988
§ 102(e) Date: Mar. 2, 1988
[87] PCT Pub. No.: WO88/64004
PCT Pub. Date: Jan. 28, 1988

[30] Foreign Application Priority Data

Jul. 15, 1986 [DE] Fed. Rep. of Germany ....... 3623826

[51] Int. Cl.$^4$ .............................................. A61K 7/135
[52] U.S. Cl. ......................................... 424/62; 424/70
[58] Field of Search ............... 424/62, 70; 8/404, 405, 8/406; 132/7; 252/94, 95, 186.28, 186.29

[56] References Cited

FOREIGN PATENT DOCUMENTS 91285 4/1896 Fed. Rep. of Germany .

*Primary Examiner*—Joseph L. Schofer
*Assistant Examiner*—Jeffrey T. Smith
*Attorney, Agent, or Firm*—Michael J. Striker

[57] ABSTRACT

A cosmetic composition having a content of hydrogen peroxide and alpha-bisabolol having the formula (I)

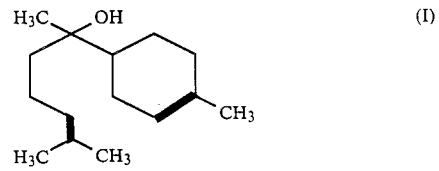

as well as the use (I) for the stabilization of hydrogen peroxide.

2 Claims, No Drawings

COSMETIC COMPOSITIONS WITH A CONTENT OF HYDROGENPEROXIDE AND ALPHA-BISABOLOL AS WELL AS USE OF ALPHA-BISABOLOL FOR THE STABILIZATION OF HYDROGENPEROXIDE

The subject of the invention is cosmetic compositions having a content of hydrogen peroxide and alpha-bisabolol having the following formula (I):

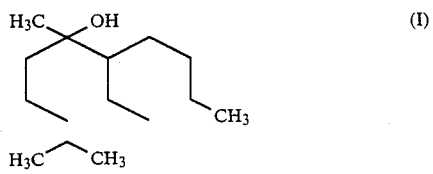

as well as the use of alpha-bisabolol for the stabilization of hydrogen peroxide.

In cosmetic compositions, hydrogen peroxide is for example used for disinfecting the skin, for oxidative hair dyeing and bleaching, and for oxidative treatment following a reductive deformation of the hair.

Hydrogen peroxide is a metastable compound and gives off oxygen when it decomposes. Oxygen has a very low solubility in water (Bunsen adsorption coefficient at 20° C.: 0.03). In closed containers, and especially over a long storage period, an overpressure can accordingly arise. This can cause part of the composition in the container to spill over in the form of foam or spray. The overpressure can also cause the container to break, and if plastic containers are used it can cause deformation or even explosions.

In cosmetic compositions containing hydrogen peroxide, it is therefore necessary to stabilize the hydrogen peroxide.

In the literature by W. Machu, "Das Wasserstoffperoxid" [Hydrogen Peroxide], Springer-Verlag (1951), pp. 197–208, a great number of stabilizers for hydrogen peroxide are described, including, among others, certain organic compounds. These compounds are found not to be completely satisfactory, however, in terms of their stabilization capability over a relatively long period of time.

From German Reich Patent No. 91 285 (to C. Raspe), it is known that among others, the terpenes thymol, menthol and camphor are capable of stabilizing solutions containing hydrogen peroxide. These compounds, however, have an unpleasant sharp odor, and in cosmetic compositions they are usable to only a very limited extent.

It is therefore the object of the invention to provide a cosmetic composition having a hydrogen peroxide content, in which the hydrogen peroxide is better stabilized than when comparable known stabilizers are used, and which does not have an unpleasant odor.

To this end it has now been found that by the use of alpha-bisabolol having the formula (I)

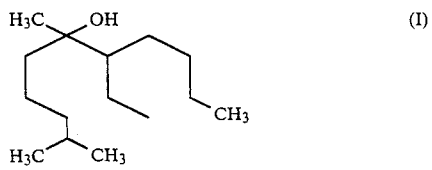

as a stabilizer of hydrogen peroxide, this object is attained in a superior manner.

Although the alpha-bisabolol is also a terpene, its capacity for stabilizing hydrogen peroxide is unexpectedly from 15 to 10 times greater than that of thymol, menthol or camphor. This property, which was unforeseeable, is documented by the comparison test in Example 1.

The alpha-bisabolol furthermore has a slightly sweet, flowery odor, so that it does not add any unpleasant odor to the cosmetic compositions.

It has also been found that the reddening of the skin and burning effects, which can arise when compositions containing hydrogen peroxide are used, is lessened by the alpha-bisabolol.

The subject of the invention is also a cosmetic compositions that contains hydrogen peroxide and alpha-bisabolol having the formula (I).

In the novel cosmetic composition, the hydrogen peroxide should be contained in a quantity of approximately 0.5 to 18% by weight, while the quantity of alpha-bisabolol is approximately 0.01 to 2.5% by weight. range from approximately 1.5 to 3.5.

In the composition according to the invention, the alphabisabolol can be contained as the sole stabilizer, or it can be contained in combination with other already known stabilizers.

Possible known stabilizers are, for example, aromatic sulfonic acids, or acid salts of strong acids, such as alkali hydrogen sulfates, acidic alkali pyrophosphates, sodium metaphosphates and alkali polyphosphates. Ascorbic acid, sulfuric acid, phosphoric acid, pyro- or polyphosphoric acid, hydrochloric acid, oxalic acid, benzoic acid, salicylic acid, malonic acid, citric acid and tannic acid, as well as phenol, thymol, paraformaldehyde, 4-acetamidophenol and phenacetin can also be included.

The novel composition can also contain tensides, on the condition that their hydrophobic components are saturated and are not oxidizable.

Suitable tensides include, above all, the following:

(a) anionic surfactive agents, such as alkali, alkaline earth, ammonium or alkanol aminic salts of alkyl sulfonates, alkyl sulfates and alkyl ether sulfates, such as sodium lauryl alcohol diglycol ether sulfate, sodium or triethanol aminic salts of alkyl sulfates having from 12 to 18 and preferably 12 to 14 carbon atoms, the sodium or triethanol aminic salts of lauryl or tetradecylether sulfates, the disodium salt of the sulfosuccinic semi-ester of alkanolamides, soaps and polyether carbonic acids, as well as (b) nonionic surfactive agents, such as ethoxylated fatty alcohols having from 12 to 18 carbon atoms, for instance lauryl, tetradecyl, cetyl and stearyl alcohol, alone or in a mixture, ethyoxylated with up to 40 moles of ethylene oxide per mole of fatty alcohol, fatty alcohols of ethoxylated lanolin or ethoxylated lanolin, polyglycolethers of alkyl phenols having from 8 to 30 carbon atoms in the alkyl radical and from 1 to 10 glycol units in the molecule, fatty acid alkanolamides, as well as etholxylated sorbitan fatty acid esters, and also (c) cationic surfactive agents, such as dilauryldimethylammonium chloride, the chlorides or bromides of alkyldimethylbenzylammonium salts, alkyltrimethylammonium salts, for example cetyltrimethylammonium chloride or bromide, tetradecyltrimethylammonium chloride or bromide, alkyldimethylhydroxyethylammonium chlorides or bromides, the dialkyldimethylammonium chlorides or bromides, alkylpyridinium salts, such as lauryl- or cetylpyridiniumchloride, alkylamidoethyltrimethylammonium ether sulfates, compounds having a cationic property such as amine oxides, for instance alkyldimethylaminoxides or alkylaminoethyldimethylaminoxides, and (d) amphoteric or dipolar surfactive agents, such as carboxyl derivatives of imidazole, N-alkyl- and N-alkylamidobetaines, N-alkylsulfobetaines, N-alkylaminopropionates, alkyldimethylcarboxymethylammonium salts having from 12 to 18 carbon atoms as well as fatty acid alkylamidobetaines, such as fatty acid aminopropyldimethylaminoacetic acid betaine.

To increase the effect of the hydrogen peroxide-containing oxidation compositions for hair treatment products, swelling and penetration agents, such as urea, 2-pyrrolidone, 1-methyl-2-pyrrolidone and dipropyleneglycolmonomethylether, can be added.

Naturally, the composition according to the invention can also contain other additives known and conventionally used for cosmetic compositions, for instance thickeners, such as kaolin, bentonite, fatty acids, higher fatty alcohols, starch, polyacrylic acid, cellulose derivatives, alginates, petrolatum or paraffin oil, as well as colorings, opacifiers, such as polyethyleneglycol esters, or alcohols, such as ethanol, propanol and isopropanol, dissolving intermediaries, stabilizers, buffer substances, perfume oils, hair conditioning or hair care ingredients such as lanolin derivatives, cholesterol or betaine. The ingredients named are used in the quantities typical for such purposes, the thickener, for example, being used in a quantity of from approximately 0.1 to 25% by weight.

The preparation can take the form of a solution, in particular an aqueous or aqueous alcoholic solution, for example, or of a creme, a gel, a paste or an emulsion.

The novel cosmetic composition can also be introduced under pressure into aerosol cans and dispensed from them in the form of a foam.

The composition according to the invention is preferably used as an oxidation agent for dyeing hair or for oxidative treatment following a reductive deformation of the hair.

In the case of hair dyeing, the novel oxidation agent is mixed with a vehicle composition containing dye immediately prior to use, and an amount sufficient for dyeing the hair is applied to the hair. After the composition is allowed to act for a period of approximately 10 to 45 minutes at approximately 15 to 50° C., the hair is rinsed with water, dried and optionally rinsed again with a weak, physiologically compatible organic acid, such as citric acid or tartaric acid.

In hair deformation, the hair is first treated with an reducing agent, for instance with an alkaline solution of a mercaptocarboxylic acid salt, and put into the desired shape, for example using curlers or by combing out. After a sufficient action period, the hair is rinsed with water, treated with the novel oxidation agent, rinsed again with water, and optionally set as needed for the final hairdo.

The following examples are intended to provide further description of the subject of the invention.

EXAMPLES OF COSMETIC COMPOSITIONS

Example 1 Oxidation composition having a pH value of 2.1 for hair dyeing or bleaching

| 0.5 g | alpha-bisabolol |
| 12.0 g | hydrogen peroxide, 50% aqueous solution |

-continued

| 2.0 g | cetylstearylalcolhol |
| 1.0 g | wool wax |
| 0.5 g | sodium lauryl sulfate |
| 0.5 g | 2-octyldecanol |
| 1.0 g | nonylphenol, ethoxylated with 10 moles of ethylene oxide |
| 0.2 g | perfume oil |
| 0.1 g | o-phosphoric acid, 85% aqueous solution |
| 82.2 g | water, completely desalinated |
| 100.0 g | |

In the above composition (1), for the comparison test, the alpha-bisabolol was replaced with an identical quantity of thymol (1a), menthol (1b) and camphor (1c), or in case (1d) the stabilizer was omitted entirely.

Storage of the compositions to be compared for three months at 40° C. and six months at 30° C. in polyethylene bottles led to identical results. They are summarized in Table 1 below.

TABLE 1

| Composition | (1) | (1a) | (1b) | (1c) | (1d) |
| --- | --- | --- | --- | --- | --- |
| Pressure | − | − | + | + | ++ |
| Loss of hydrogen peroxide in % (relative to the initial content) | 0.5 | 2.5 | 5 | 3 | 11 | where
− stands for no overpressure
+ stands for overpressure
++ stands for severe overpressure The loss of hydrogen peroxide was determined by titration with thiosulfate/iodine.

The above comparison test demonstrates the substantially better stabilizing action of the alpha-bisabolol for hydrogen peroxide, as compared with thymol, menthol and camphor.

Example 2 Composition having a pH value of 2.5 for oxidative treatment following a reductive permanent wave

| 6.0 g | sodium lauryl ether sulfate, ethoxylated with 2 moles of ethylene oxide per mole of lauryl alcohol |
| 0.1 g | alpha-bisabolol |
| 5.0 g | hydrogen peroxide, 50% aqueous solution |
| 0.1 g | hippuric acid |
| 1.0 g | nonylphenol, ethoxylated with 10 moles of ethylene oxide |
| 1.0 g | citric acid |
| 86.8 g | water, completely desalinated |
| 100.0 g | |

After storage for 3 to 6 months, respectively, no overpressure was found.

Example 3 Composition having a pH value of 2.8 for oxidative treatment following a reductive permanent wave

| 0.01 g | alpha-bisabolol |
| 4.0 g | hydrogen peroxide, 50% aqueous solution |
| 2.0 g | fatty acid amidopropyldimethylaminoacetic acid betaine, 30% aqueous solution |
| 0.5 g | lauryldimethylaminoxide |
| 0.2 g | ethylenediaminotetraacetic acid |
| 0.05 g | phenacetin |
| 0.2 g | sodium dihydrogen phosphate |
| 93.0 g | water, completely desalinated |

| |
|---|
| 100.0 g |

After storage for 3 months and 6 months, respectively, no overpressure was found.

Example 4 Oxidation composition having a pH value of 2.2 for hair dyeing or bleaching

| |
|---|
| 2.5 g alpha-bisabolol |
| 24.0 g hydrogen peroxide, 50% aqueous solution |
| 3.0 g nonylphenol, ethoxylated with 10 moles of ethylene oxide |
| 0.1 g o-phosphoric acid, 85% aqueous solution |
| 70.4 g water, completely desalinated |
| 100.0 g |

After storage for 3 months and 6 months, respectively, no overpressure was found.

Example 5 Composition having a pH value of 2.5 for oxidative treatment following a reductive hair relaxation

| |
|---|
| 0.5 g alpha-bisabolol |
| 4.0 g hydrogen peroxide, 50% aqueous solution |
| 2.0 g coconut fatty acid monoethanolamide |
| 10.0 g lauryl alcohol diglycolether sulfate sodium salt, 28% aqueous solution |
| 0.5 g perfume oil |
| 83.0 g water, completely desalinated |
| 100.0 g |

After storage for 3 months and 6 months, respectively, no overpressure was found.

Unless otherwise indicated, all percentages given herein refer to percents by weight.

We claim:

1. A cosmetic composition which contains from 0.5 to 18% by weight hydrogen peroxide and from 0.01 to 2.5% by weight alpha-bisabolol.

2. A cosmetic composition as defined in claim 1 characterized in that the pH value is from 1.5 to 3.5.

* * * * *